(12) United States Patent
Sairam et al.

(10) Patent No.: US 8,241,645 B2
(45) Date of Patent: Aug. 14, 2012

(54) VACCINE

(75) Inventors: Mustoori Sairam, New Delhi (IN); Anju Bansal, New Delhi (IN); Sarada S. Surya Kumari, New Delhi (IN); Piyush Paliwal, New Delhi (IN)

(73) Assignee: The Director General, Defence Research and Development Organisation, New Delhi (IN)

( * ) Notice: Subject to any disclaimer, the term of this patent is extended or adjusted under 35 U.S.C. 154(b) by 337 days.

(21) Appl. No.: 11/992,932

(22) PCT Filed: Oct. 4, 2006

(86) PCT No.: PCT/IN2006/000396
§ 371 (c)(1),
(2), (4) Date: Apr. 22, 2010

(87) PCT Pub. No.: WO2007/039917
PCT Pub. Date: Apr. 12, 2007

(65) Prior Publication Data
US 2010/0196416 A1    Aug. 5, 2010

(30) Foreign Application Priority Data

Oct. 4, 2005 (IN) .......................... 2648/DEL/2005
Oct. 4, 2005 (IN) .......................... 2650/DEL/2005

(51) Int. Cl.
*A61K 39/112* (2006.01)
*A61K 38/00* (2006.01)
*C12N 1/00* (2006.01)

(52) U.S. Cl. .... 424/258.1; 424/9.1; 424/9.2; 424/184.1; 424/234.1; 435/243; 435/252.8; 530/300; 530/350

(58) Field of Classification Search ................... 424/9.1, 424/9.2, 184.1, 234.1, 258.1; 435/243, 252.8; 530/300, 350
See application file for complete search history.

(56) References Cited

OTHER PUBLICATIONS

Barrios C. et al.: "Heat Shock Proteins as Carrier Molecules: In Vivo Helper Effect Mediated by *Escherichia coli* Groel and DNAK Proteins Requires Cross-Linking with Antigen"; Clinical and Experimental Immunology, Oxford, Gb, Vo198, No. 2, Nov. 1994, pp. 229-233, XP000965591 ISSN: 0009-9104 The Whole Document.
Ensgraber M et al.: "A 66-Kilodalton Heat Shock Protein of *Salmonella-typhimurium* is Responsible for Binding of the Bacterium to Intestinal Mucus" Infection and Immunity, vol. 60, No. 8, 1992, pp. 3072-3078, XP002413015 ISSN: 0019-9567, p. 3073, col. 2.
Chander Harish et al.: "Reactivity of Typhoid Patients Sera with Stress Induced 55 kDa Phenotype in *Salmonella enterica* serovar typhi" Molecular and Cellular Biochemistry, vol. 267, No. 1-2, Dec. 2004, pp. 75-82, XP002413016 ISSN: 0300-8177, p. 77, col. 1, last paragraph.

*Primary Examiner* — Rodney P. Swartz
(74) *Attorney, Agent, or Firm* — Ladas & Parry LLP

(57) ABSTRACT

A typhoid vaccine using heat shock protein (Hsp) of *Salmonella typhi* and a method for the manufacture thereof. A composition comprising an effective amount of a complex of a Hsp, in part or whole, either alone or covalently or non-covalently bound to an antigenic molecule, which when administered to a mammal elicits specific immunological responses in the host. The antigenic molecule refers to the exogenous antigens/immunogens such as viz LPS, peptide, nucleic acid or polysaccharide or antigenic/immunogenic fragments and derivatives thereof.

12 Claims, 5 Drawing Sheets

VACCINE

Figure 1:
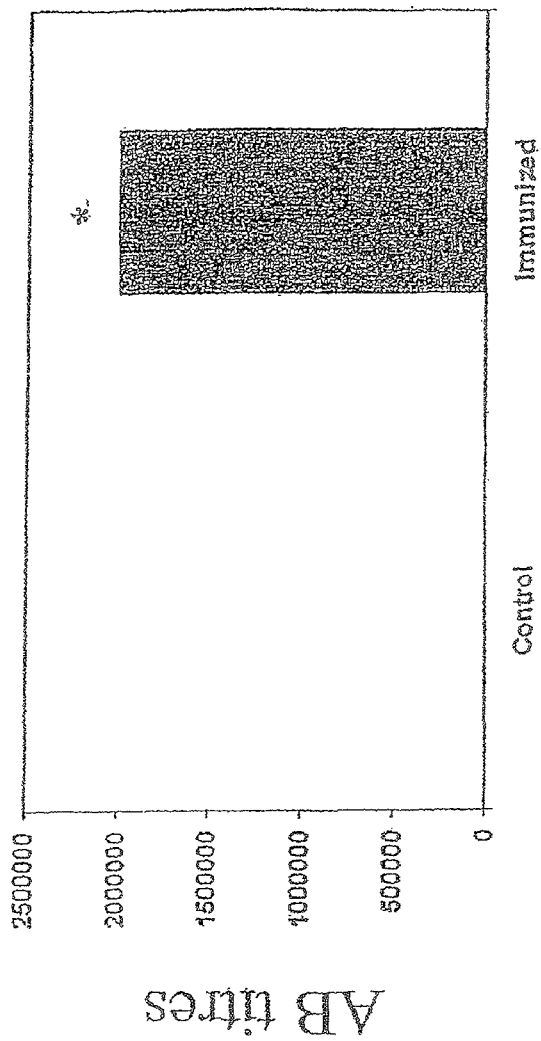

This application is a 371 out of International Application PCT/IN2006/00396, filed Oct. 4, 2006, which claims the benefit of Indian Patent Application 2648/DEL/2005 filed Oct. 4, 2005, and Indian Patent Application 2650/DEL/2005, filed Oct. 4, 2005.

FIELD OF INVENTION

The present invention relates to the development of typhoid vaccine using heat shock proteins 60 (Hsp60) and Hsp70 of *Salmonella typhi*. The method of invention involves administering a composition comprising an effective amount of a complex consisting of a Hsp, in part or whole, either alone or covalently or non-covalently bound to an 'antigenic molecule', which when administered elicits specific immunological responses in the host. 'Antigenic molecule' used herein refers to the exogenous antigens/immunogens viz lipopolysaccharides (LPS), peptide, nucleic acid or polysaccharide or antigenic/immunogenic fragments and derivatives thereof.

The present invention relates to the development of typhoid vaccine using heat shock proteins 60 (Hsp60) and Hsp70 of *Salmonella typhi*. The method of invention involves administering a composition comprising an effective amount of a complex consisting of a Hsp, in part or whole, either alone or covalently or non-covalently bound to an 'antigenic molecule', which when administered elicits specific immunological responses in the host. 'Antigenic molecule' used herein refers to the exogenous antigens/immunogens viz lipopolysaccharides (LPS), peptide, nucleic acid or polysaccharide or antigenic/immunogenic fragments and derivatives thereof.

BACKGROUND OF INVENTION

Typhoid fever, caused by the gram negative bacterium *Salmonella enterica* serovar typhi, is closely associated with poor food hygiene and inadequate sanitation. After ingestion of contamination food and water, Salmonellae are able to penetrate the gut epithelium through specialized microfold cells (M cells) lining the Peyer's patches (Jones et al, 1994, J. Exp. Med., 180, 15-23). After crossing this intestinal barrier, bacteria are able to spread rapidly to visceral tissues, including liver and spleen, where they reside primarily in tissue macrophages. After 5-21 days of incubation, the patients experience fatigue, headache, abdominal pain and fever, constipation or diarrhea. Severe forms may entail cerebral dysfunction, delirium and shock and occasionally intestinal perforation and hemorrhage. *S. typhi* is a host restricted pathogen causing typhoid fever in humans. However, it is avirulent in susceptible strains of mice. In contrast, other *Salmonella* serovars, specifically *S. typhimurium, S. dublin, S. enteritidis*, which are lethal in mice, usually do not cause a disseminated, systemic disease in humans but clinically manifest as gastroenteritis and diarrhea in humans (Fang 1991, Medicine 70, 198-207; Jones 1996, Annu. Rev. Immunol. 14, 533-561). Infection of susceptible mice with *S. typhimurium* provides a murine model for typhoid fever which bears many similarities to human serovar typhi infection.

According to WHO, the annual global incidence of typhoid fever is 0.3%, corresponding to about 16 million cases, of which approximately 600,000 result in death. Incidence of typhoid fever peaks between the ages of 5 and 12 years in endemic areas. In recent years *S. typhi* has gradually acquired resistance to oral antibiotics; chloramphenicol, trimethoprim-sulfamethoxazole, ampicillin and tetracycline. Non availability of relevant drugs and rapid development of microbial drug resistance have led to the need of efficacious and affordable vaccines to control typhoid fever. The old inactivated whole cell typhoid vaccines are highly reactogenic, causing high typhoid fever, pain in abdomen, vomiting and diarrhea. Also, these vaccines are only up to 70% effective and the immunity does not persist for more than 3-5 years (Hornick et al 1967, Med. Clin. North. Am. 51, 617-23; Ivanoff et al 1994, Bulletin of the World Health Organization. 72: 957-971).

Immunological protection against typhoid fever requires both cell mediated and humoral responses. Specific cytotoxic T lymphocytes (CTL) have been demonstrated after oral vaccination with live attenuated *S. typhi*, indicating a role for CTLs in the defense against typhoid fever. Infection is bimodal process determined by host and pathogen. During infection, pathogen as well as host is confronted with various stressful conditions and to protect against these, both increase the synthesis of stress proteins (SPs). Hsps or Sps are highly conserved, ubiquitous and abundant proteins produced by all prokaryotic and eukaryotic cells in response to a variety of physiological insults like heat, hypoxia, nutrient deprivation, oxygen radicals, viral infection, etc. (Morimoto and Milarski, 1990, Stress proteins in Biology and medicine, Cold Spring Harbour, N.Y.; Young 1990, Stress proteins in biology and medicine, Cold Spring Harbour, N.Y.). They ensure survival under stressful conditions that, if left unchecked, would lead to irreversible cell damage and ultimately to cell death. Although they are classified as Sps, Hsps also have essential functions in the cell under normal growth conditions. They are involved in the synthesis, folding, assembly and disassembly of protein complexes and also assist in translocation of proteins from one compartment to another and are often referred to as Molecular chaperones (Ang et al 1991, J. Biol. Chem., 266, 24233-24236; Gething and Sambrook 1992, Nature 355, 33-45, Rothman, 1989, Cell, 59, 591-601). They are divided into a series of families based on their molecular mass in kilodaltons. Hsps 60, 70 and 90 are generally found in cytosol and mitochondria. Gp96 and calreticulum are located in the endoplasmic reticulum.

The Hsps are also involved in several molecular processes of the immune system, such as immunoglobulin chain assembly (Haas 1991, Curr Top Microbiol Immunol 167, 71-92), antigen processing and presentation (Pierce et al, 1991, Curr Top Microbiol Immunol 167, 83-92) and the assembly of functional major histocompatibility complexes I and II (De Nagel and Pierce 1993, Crit. Rev. Immunol. 13, 71-81). Microbial Hsps are dominant antigens for the host immune response to a variety of pathogens including bacteria, fungi, helminthes and protozoan parasites (Young and Elliot 1989, Cell, 59, 5-8) and the immune recognition of Hsp of pathogens serves as a first line of defense. Although the abundance of Hsps may explain why they behave as dominant antigens, it is surprising that the immune system focuses its attention on these proteins which are so highly conserved (bacterial and mammalian Hsps have 50% homology at amino acid level). Most people don't develop dangerous autoimmune responses to self Hsps, although they do posses T cells which recognize these self Hsps, suggesting that these cells are highly regulated (Schawartz 1989, Cell 57, 1073-1081). However, some studies suggest that autoimmune diseases like arthritis may develop through inappropriate cross-reactivity with self Hsp (Young 1990 Ann Rev Immunol 8, 401-420).

The finding that the GroEL complex is involved in bacterial cell wall synthesis, suggests the ready accessibility of these Hsp molecules to antibodies (McLennan and Masters 1998, Nature 392,139). Some studies have suggested the presence of Hsp70 also on the bacterial surface and the heat shock response appears to mediate adhesion to the host cell. Immunologic memory for cross-reactive determinants of conserved Hsp is generated during life, based on frequent re-stimulation by subsequent encounters with microbes with different degrees of virulence. Under these conditions, infection of an individual with a virulent pathogen would enable the already prepared immune system to react quickly before the immune response to more pathogen-specific antigens develops. An immune response to conserved determinants of Hsp shared by different microbes may, furthermore, prevent colonization of the host by microbial pathogens. Several lines of evidence indicate that Hsp also represent unique targets for $\gamma\delta T$ cells (Fu et al, 1994, J. Immunol 152, 1578-1588)

In mycobacterial infections, reactivity to Hsp predominates, with Hsp60 as an immunodominant target of the antibody and T-cell response in mice and humans. Hsp60-specific antibodies have been detected in patients with tuberculosis and leprosy, and also in mice after infection with *M. tuberculosis* (Shinnick 1991, Curr Top Microbiol Immunol 167, 145-160). In patients with leprosy or in persons vaccinated with *M. bovis* BSG, CD4$\alpha\beta$T cells specific for the mycobacterial Hsp60 have been found (Mustafa et al 1993, Infect Immun 61, 5294-5301). This finding points to an important role for Hsp60-specific T cells in mycobacterial infection. In vitro stimulation of murine splenocytes and immunization of mice with mycobacterial Hsp60 induced the expansion of CD8$\alpha\beta$T cells specific for mycobacterial Hsp60 (Zugel and Kaufmann 1997, Infect. Immun, 65, 3947-3950).

Immune responses to Hsp60 are also frequently found in other microbial infections. In a murine model of yersiniosis, numbers of CD4$\alpha\beta$T cells specific for Hsp were increased in infected animals and mediated significant protection against infection with *Yersinia enterocolitica* when adoptively transferred. Similarly, in infants, levels of antibodies against Hsp60 were significantly increased after vaccination with a trivalent vaccine against tetanus, diphtheria, and pertussis (Del Giudice et al 1993, J Immunol 150, 2025-2032). These findings further suggest that priming of the immune system to Hsp60 is a common phenomenon, occurring at an early stage of life.

Similarly increased antibody levels to Hsp70, have been identified in sera of patients suffering from malaria, leishmaniasis, schistosomiasis, filiariasis, and candidiasis (Shinnick 1991, Curr Top Microbiol Immunol 167, 145-160). In contrast to Hsp60, responses to pathogen-derived Hsp70 seem to be more restricted, sometimes exclusively species specific. Shinnick (1991) demonstrated an important role of the humoral response against Hsp90 in systemic candidiasis. The Hsp90-specific antibodies contributed directly to protection against *Candida albicans* infection (Matthews and Burnie 1992, Immunol Today 133, 345-348).

Today Hsps are the object of intense work by scientists all over the world as a potential means of vaccines to treat cancer and other diseases. In modern medicine, immunotherapy or vaccination has virtually eradicated diseases such as polio, tetanus, tuberculosis, chicken pox, measles, hepatitis, etc. The approach using vaccinations has exploited the ability of the immune system to prevent infectious diseases. Such vaccination with non-live materials such as proteins generally leads to an antibody response or CD4+ helper T cell response (Raychaudhuri and Morrow 1993, Immunol Today 14, 344-348). On the other hand, vaccination or infection with live materials (live cells or infectious viruses) generally leads to a CD8+ cytotoxic T lymphocyte (CTL) response. A CTL response is crucial for protection against cancers, infectious viruses and bacteria. This poses a practical problem, for, the only way to achieve a CTL response is to use live agents which are themselves pathogenic. The problem is generally circumvented by using attenuated viral and bacterial strains or by killing whole cells which can be used for vaccination. These strategies have worked well but the use of attenuated strains always carries the risk that the attenuated reagent may recombine genetically with the host DNA and turn into a virulent strain. Thus, there is need for methods which can lead to CD8+ CTL response by vaccination with non-live materials such as proteins in a specific manner.

Hsps as vaccines are a novel approach to disease prevention. Epitope analysis indicates the presence of multiple B and T cell epitopes in many of these Hsps. They can be used as carriers, vectors and in that regard offer a promising future. There is now substantial evidence that native Hsps (Hsp70, gp96, calreticulum) isolated from tumors can be used as adjuvant free anti tumor vaccines in animal models (Suto and Srivastava 1995, Science, 269, 1585-1588). Srivastava et al (1991, Curr Top Microbiol Immunol 167, 109-123) have demonstrated that immunization of mice with gp96 or Hsp70 isolated from a particular tumor, rendered the mice immune to that particular tumor but not to antigenically distinct tumors whereas corresponding preparations from normal tissues did not grant immunity. Further studies have revealed that Hsps are closely associated with peptides and Hsp depleted of peptides was found to lose its immunogenic activity. The ability of Hsps to potentially bind to the whole cellular peptide repertoire makes them attractive candidates for cancer vaccines. The immunogenic properties of Hsp have been demonstrated in particular for *Mycobacterium tuberculosis* Hsp70, which has been used successfully as an adjuvant free carrier molecule (Barrios et al, 1992, Eur J Immunol 22, 1365-1372). Suzure and Young (1996, J Immunol 156, 873-879) further demonstrated that in the absence of adjuvants, covalent linking of *M. tuberculosis* Hsp70 to human immunodeficiency virus type 1 p24 elicited humoral and cellular immune responses to p24, when mice were immunized with this recombinant fusion protein. Most vaccines require adjuvants to provoke effective and protective immune responses, where as Hsp70 fusion proteins induced these immune responses without adjuvants. Most adjuvants used in research cause powerful and unpleasant side effects in humans. Thus only alum, a very weak adjuvant is used in human vaccines.

Hsp fusion proteins elicit antigen specific CTL responses in the absence of adjuvants. Immunization of mice with a soluble fusion protein, consisting of an ovalbumin fragment, a well characterized T cell antigen, covalently linked to mycobacterial Hsp70, induced a strong MHC class I-restricted CD8 T-cell response against a dominant ovalbumin T-cell response against a dominant ovalbumin T-cell epitope and partially protected mice from tumor challenge (Suture et al, 1997, Proc Natl Acad Sci USA 94, 13146-13151). Hsp fusions appear to gain access to MHC class I processing and presentation pathway in a non classical manner. This was unexpected as immunization with soluble proteins, especially in absence of adjuvans, rarely elicit CTL responses. Huang et al (2000, J Exp Med 191, 403-408) showed the ability to elicit CTL is independent of CD4+ lymphocytes, and this function resides in a 200 amino acid domain of Hsp70, concluding that the ability of the fusion proteins to elicit CD8+ T cell does not depend on the Hsps' chaperone properties. They further demonstrated that ovalbumin (OVA) Hsp70 fusion proteins with murine homologue of TB Hsp70 (m Hsp70) also elicited CTL responses equivalent to those generated by mycobacterial Hsp70 fusion protein and was also independent of CD4. This shows that both mycobacterial and murine (self) Hsp70 enhance immune responses.

Numerous studies have documented antibody responses to *S. typhi* proteins, and the major antigenic components include the somatic 0 antigen (endotoxin, lipopolysaccharide), flagellar H antigen, Vi antigen and outer membrane proteins). In contrast very little is known about host immune response to *Salmonella* Hsps. The pathogenesis of typhoid fever and the role of various components of the human immune response to *Salmonella typhi* remain poorly understood. There is little information about *S. typhi* Hsps and genes which may be involved in virulence or which are important in eliciting a host immune response. The ability of heat shock proteins to chaperone peptides, including antigenic peptides, interact with antigen presenting cells (APC) through a receptor, stimulating antigen (Ag) presenting cells to secret inflammatory cytokines and mediate motivation of dendritic cells, makes them a unique starting point for generation of immune responses. These properties permit the use of Hsps for development of a new generation of prophylactic and therapeutic vaccines against infections agents.

The old inactivated whole cell typhoid vaccines are highly reactogenic, causing high typhoid fever, pain in abdomen, vomiting and diarrhea. In many countries these have been replaced by two currently licensed vaccines: purified Vi polysaccharide parenteral vaccine and Ty 21a, used as a live oral vaccines: purified Vi polysaccharide parenteral vaccine and Ty 21a, used as a live oral vaccine. Ty21a, a mutant *S. typhi* strain, was isolated by Germanier et at (1982, Bacterial vaccines, pp 419-421. vol 4, New York, USA) and has been used as an orally administered, live, attenuated vaccine. It is in the form of capsules, 3 capsules given orally on alternate days and the capsules need to be swallowed intact. Though the vaccine is effective after 2 years of age, practically a child above 4-6 years of age can swallow capsules. Hence it is recommended after the age of 4-6 years. It is contraindicated in immune compromised host as it is a live vaccine. However, this strain Ty21a has lost an epimerase capable of converting glucose to galactose, a loss resulting in defective synthesis of the polysaccharide component of LPS. As a result Ty21a is not well adapted to survive and multiply in the intestinal tract (Gilman et al, 1977, J. Infect. Dis. 136: 717-23).

These days a parenteral vaccine, which is made of purified Vi capsular polysaccharide, is being widely used. Vi polysaccharide is a well standardized antigen that is effective in a single subcutaneous or intramuscular dose and is safer than whole cell vaccine. But this vaccine can be given only after completing 2 years of age and it confers protection seven days after injection. Besides, it can lead to side effects like pain, swelling, redness, tenderness, etc. and sometimes mild fever lasting for 24 hours. The protective efficacy lasts for 2-3 years in most of the vaccines. Hence one has to revaccinate every three years. Hsps as vaccines are a novel approach to disease prevention.

Srivastava in U.S. Pat. No. 6,410,028 has described the methods of prevention and treatment of cancer and infectious disease by the administration of complexes of human Hsp-antigen molecules to individuals but there is little information about *S. typhi* proteins and genes which may be involved in virulence or which are important in eliciting a host immune response.

The Hsp based vaccines, unlike other recombinant protein based vaccines, stimulate both humoral and cell mediated immune responses and are currently not available against microbial infections. The present invention, therefore, relates to the development of microbial Hsp based Recombinant vaccine for the prevention of typhoid fever in humans. DnaK (Hsp70) or GroEL protein (Hsp60) of *S. typhi* either alone or in combination with antigenic molecules is used in the present invention as a vaccine to augment the immune response against *S. typhi* in mice.

OBJECTS OF THE INVENTION

The main object of the present invention is to develop a potent and cost effective vaccine against typhoid fever and salmonellosis using GroEL proteins of *S. typhi* which obviates the drawbacks detailed above.

Another object of the present invention is to develop a potent and cost effective vaccine against typhoid fever and salmonellosis using DnaK (Hsp70) protein of *S. typhi* which obviates the drawbacks detailed above.

Further object of the present invention is to use the immunogenicity of GroEL or DnaK proteins by conjugating it with other antigenic molecules.

Still another object of the present invention is to use exogenous antigens/immunogens viz LPS, peptide, nucleic acid or polysaccharide or antigenic/immunogenic fragments and derivatives thereof as antigenic molecules.

Yet another object of the present invention is to evaluate the immune response of the vaccine in animals and humans.

Still another object of the present invention is to challenge animals with *S. typhimurium* to study the efficacy of GroEL or DnaK after booster immunization with the vaccine.

SUMMARY OF THE INVENTION

The present invention provides a cost effective vaccine against typhoid fever and salmonellosis using Hsp either alone or bound to an antigenic molecule that elicits immunological responses in animals and humans.

In one embodiment of the present invention the Hsp is selected from one or more of GroEL or DnaK protein of *Salmonella typhi* and their closely related serovars.

In another embodiment of the present invention the Hsp is bound to the antigenic molecule covalently or non-covalently.

In yet another embodiment of the present invention the antigenic molecule is exogenous antigen or immunogen selected from a group consisting of lipo-polysaccharides, peptides, nucleic acids, polysaccharides, antigenic fragments, immunogenic fragments and derivatives thereof.

In still another embodiment of the present invention the vaccine is administered to humans or animals in an amount in the range of 1-100 µg/kg BW.

In yet another embodiment the present invention describes a method of vaccinating animals and humans consisting of administering a pharmaceutical acceptable quantity of vaccine, sufficient to elicit an immune response in animals and humans.

The present invention also provides a pharmaceutical composition comprising an effective amount of vaccine and one or more pharmaceutically acceptable additives.

In another embodiment of the invention, the pharmaceutically acceptable additives are selected from the group consisting of carriers diluents, stabilizing agents, solvents, flavoring agents and the like.

BRIEF DESCRIPTION OF THE ACCOMPANYING DRAWINGS

FIG. 1: Effect of GroEL vaccination on immune response in mice.

Figure 2:
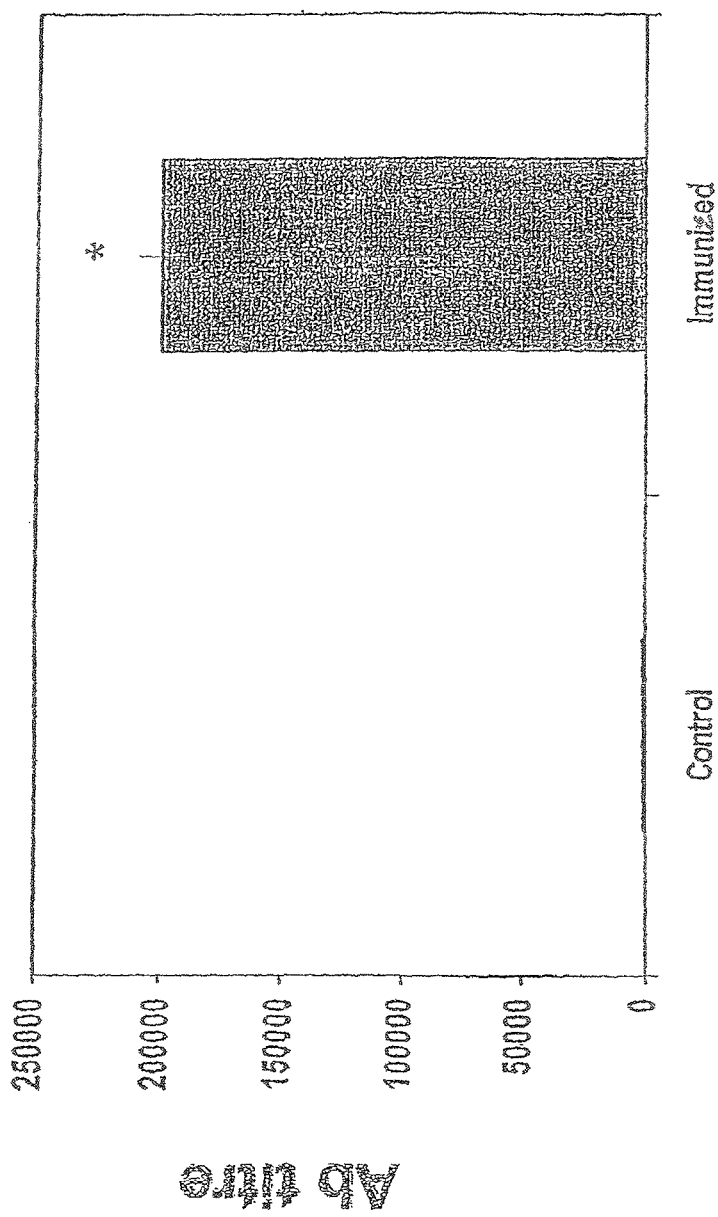

FIG. 2: Effect of DnaK of S. typhi vaccination on immune response in mice.

Figure 3:
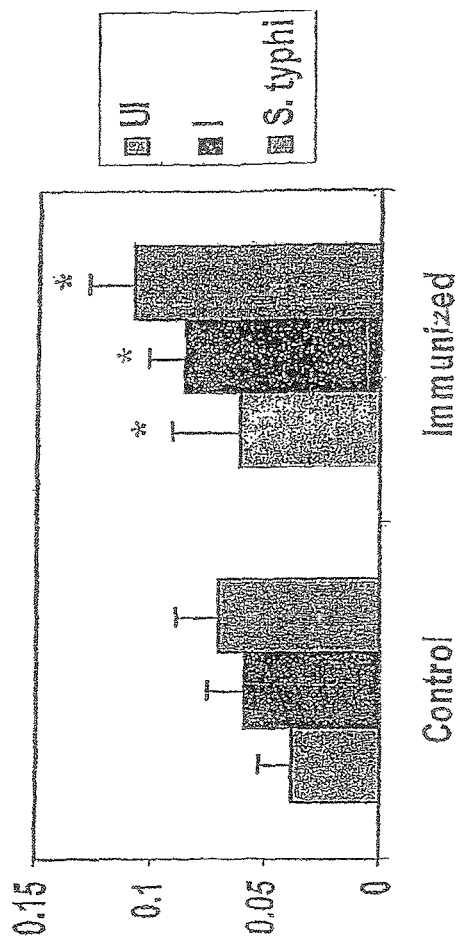

FIG. 3: Effect of GroEL vaccination on lymphocyte proliferative response.

Figure 4:
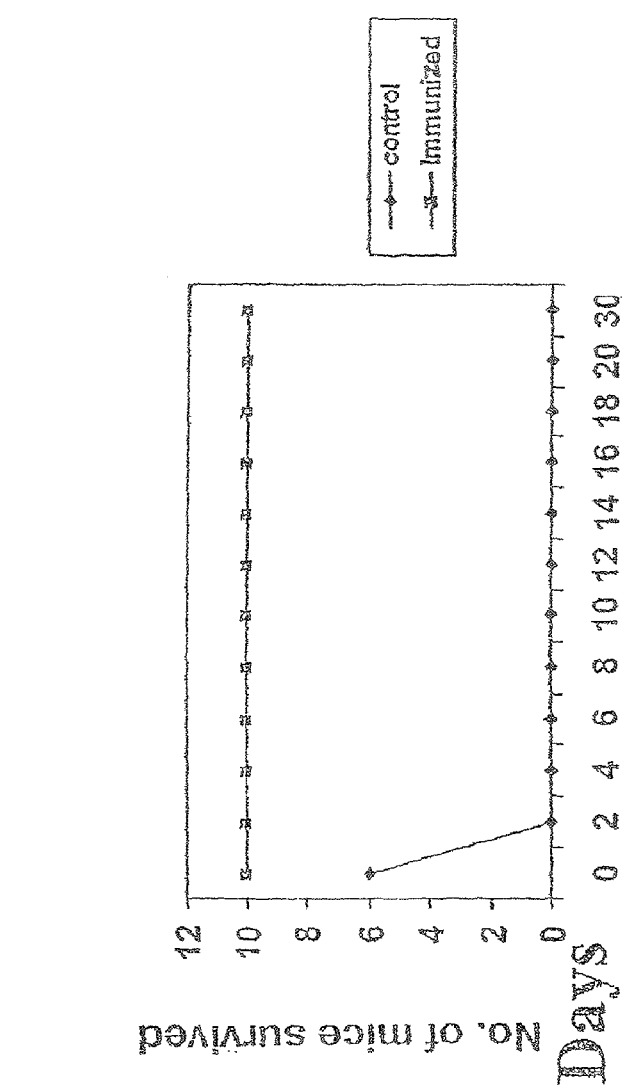

FIG. 4: Effect of DnaK of S. typhi vaccination on survival of mice.

Figure 5:
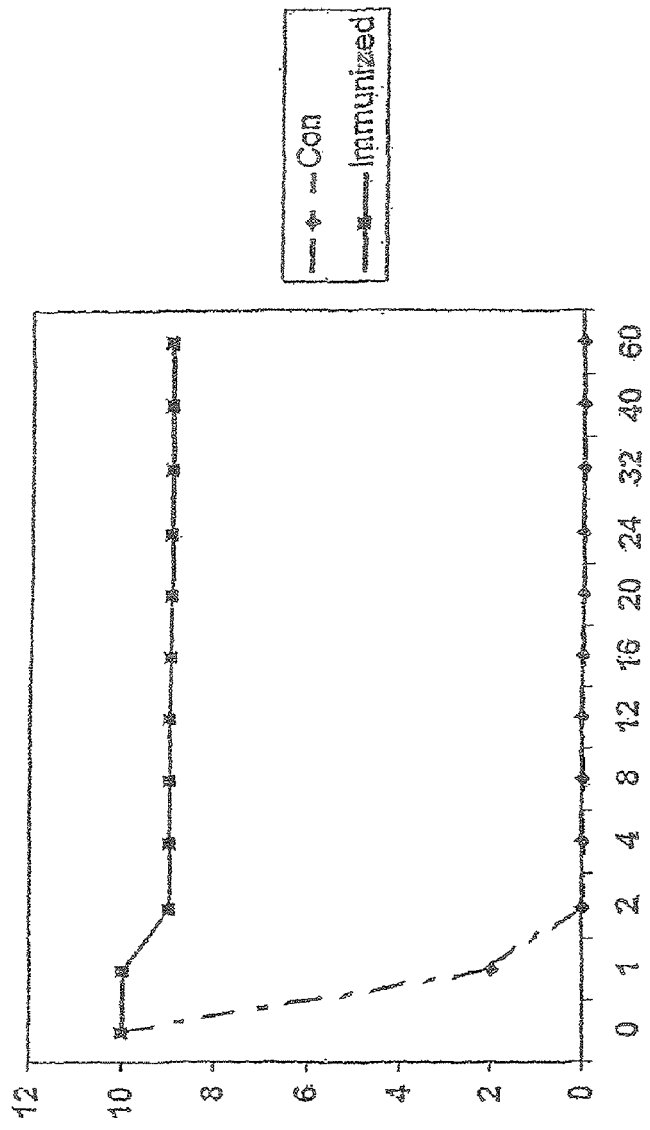

FIG. 5: Effect of GroEL vaccination on survival of mice challenged with lethal dose of S. typhimurium.

DETAILED DESCRIPTION OF THE INVENTION

The Genomic DNA is isolated from the overnight grown culture of Salmonella typhi using Genomic DNA isolation kit. GroEL/DnaK gene is amplified by Polymerase Chain Reaction (Taq:Pfu, 1:1) using primers designed in the lab. Conditions of PCR are: 95° C. for 5 minutes (Pre heating lid), 95° C. for 1 minutes (denaturation), 55° C. for 1 minutes (annealing), 72° C. for 90 sec. (extension) for total 36 cycles. The PCR product is purified by PCR DNA purification kit. DNA bound to a silica membrane of the spin column is washed and eluted in the Tris buffer.

pQE Vector:

pQE-30 expression vector is a high copy number plasmid of 3.4 kb in size. It combines a powerful phage T5 promotor (recognized by E. coli. Polymerase) with a double lac operator repression module to provide tightly regulated expression of recombinant proteins in E. coli. Protein synthesis is effectively blocked in the presence of high levels of lac repressor and the stability of cytotoxic constructs is enhanced. It has 6×His tag coding sequence at 5' end of the polylinker cloning region and thus enables the placement of 6×His tag at N-terminus of the recombinant protein. β-lactamase gene confers ampicillin resistance which serves as a marker for selection of recombinants.

Plasmid DNA of pQE-30 expression vector is isolated by kit as per manufacturer's instructions. An overnight grown E. coli culture is harvested by centrifugation and subjected to modified alkaline SDS lysis procedure followed by absorption of DNA onto silica in the presence of high salts. Contaminants are removed by washing and the bound DNA is eluted in distilled water (DW) or Tris EDTA (TE) buffer.

Restriction Digestion:

The PCR product and pQE-30 plasmid DNA are restricted with Bam HI and Hind III to generate cohesive ends and purified by spin column.

Ligation and Transformation:

The PCR product of DnaK/GroEL and pQE-30 vector DNA are then ligated at 16° C. overnight, using T4 DNA ligase. Transformation is carried out with ligated products using E. coli DH 5α cells and the resultant transformants are selected on Ampicillin plates.

Recombinants obtained are screened for the presence of desired insert by restriction digestion and PCR followed by DNA sequencing. The recombinant plasmids are isolated and subsequently introduced into an expression strain of E. coli BL-21 (DE-3) by electroporation. Briefly, electrocompetent cells of BL-21 are prepared and electric shock of 1500 V is given to the mixture of cells in a medium containing recombinant plasmid. DNA transformants are selected on ampicillin plates.

Expression of Proteins:

GroEL (Hsp 60)/DnaK (Hsp 70) gene cloned in BL-21 cells is induced with varying concentrations of isopropyle-hiogalactoside (IPTG) (0.5 mM to 4 mM) for varying time period (1 hr to 4 hr). Briefly overnight grown cultures of recombinant colonies obtained above are re-inoculated and allowed to grow till O.D.$_{600}$ reaches 0.5-0.6. Cultures in this logarithmic phase are induced with IPTG (0.5 mM to 4 mM) for 1 to 4 hrs. After induction, cells are lysed in sample buffer and analyzed by SDS-PAGE.

Localization and Isolation of Recombinant Protein in Induced Cells:

To determine the solubility of GroEL/DnaK protein, induced cells (OD$_{600}$~1.0) are first lysed in native lysis buffer (50 mM Tris HCl, 200 mM NaCl, pH 7.5, 1 mM phenyl methyl sulfonyl fluride (PMSF)) and incubated on ice for 30 min, followed by sonication on ice to lyse the cells. Lysate is then centrifuged at 15,000 g for 20 min and the resulting supernatant (S1) is transferred into a fresh tube. To the pellet, urea lysis buffer (50 mM Tris, HCl, 200 mM NaCl, 5M urea, pH 7.5, 1 mM PMSF) is added and again sonicated as before. Supernatant (S2) is collected after centrifugation. Both the fractions, native lysate supernatant S1 and urea lysate supernatant S2 are analyzed by SDS PAGE. The protein band is observed in soluble phase S1. This is confirmed by Western blotting using anti-histidine (anti-His) antibody as primary antibody and Rabbit antimouse IgG/HRP conjugate as secondary antibody.

Purification of Recombinant GroEL/DnaK Protein:

The recombinant GroEL/DnaK protein is purified by Nickel-nitrilotriacetate (Ni-NTA) chromatography under denaturing conditions followed by arginine mediated refolding. Briefly, the protein sample is added to the charged gel and allowed to bind to the gel for 30 min at room temperature with gentle agitation. Gel is sedimented by centrifugation at 500 g for 2-5 minutes and the supernatant is carefully decanted. The gel is washed with wash buffers I (20 mM, Na$_2$HPO$_4$; 0.5 M NaCl; 20 mM Imidazole; 8M urea) and II (20 mM, Na$_2$HPO$_4$; 0.5 M NaCl; 20 mM Imidazole; 8M urea). The protein is then finally eluted with elution buffer containing 20 mM, Na$_2$HPO$_4$; 0.5 M NaCl; 0.5 M Imidazole; 5M urea.

After purification, the protein is refolded in refolding buffer. Refolding is initiated by rapid dilution and is then incubated for 24 h at 4° C. without stirring. The refolded preparation is dialyzed extensively to eliminate arginine and urea, against dialysis buffer containing 50 mM Tris and 1 mM EDTA for 24 h, with buffer changes every 12 h. The dialyzed sample is centrifuged and concentrated by AMICON filtration.

Immune Response:

The immune response of recombinant GroEL/DnaK is evaluated by injecting 50 μg protein/mouse, intraperitonially on 0, 7th and 28th day. Seven days after the last injection, the mice are scarified, serum is collected for antibody titre and the splenocytes is cultured for determining cell mediated responses. Antibody titre is determined by ELISA using commercially available 96-well microtitre plates. The titres >0.2 OD and above are taken as positive for scoring. A significant increase in antibody titres (>2,000,000) is observed in animals immunized with GroEL/DnaK after third immunization (FIGS. 1 and 2).

Splenocytes from immunized mice show significant increase in proliferation (FIG. 3) and in γ-IFN and IL-4 production. The study reveals that GroEL protein is highly immunogenic and stimulates both B and T lymphocytes.

Challenge and Protection Studies:

The study has the approval of Ethics Committee of the Institute. Animal experiments are conducted according to principles set forth in the Declaration of Helsinki and in the Guide for the Care and Use of Laboratory animals. Eight to Twelve week old female BALB/c mice are used in all cases. S. typhi is a host restricted pathogen causing typhoid fever in humans only. It does not cause disease in mice, whereas S. typhimurium which causes mild gastroenteritis in humans, is lethal in mice (oral $LD_{50}$ of 104 organisms and intraperitonial $LD_{50}$<50 to 1.6×10$^2$). Thus, infection of mice with *S. typhimurium* provides a murine model for typhoid fever as it bears many similarities to human serovar typhi infection.

A group of 10 mice are vaccinated with GroEL/DnaK protein (50 µg/mouse) on 0, 7$^{th}$ and 28$^{th}$ day. Two weeks after the last booster immunization, both control and vaccinated mice are challenged with *S. typhimurium* intraperitonially (1×10$^i$ cells ml). The mice are monitored daily after infection for at least 2 months. There is 100% death in control mice after challenge with *S. typhimurium* within 48 hrs. However, all the mice vaccinated with DnaK survive the lethal infection of *S. typhimurium* even 60 days after challenge (FIG. 4). Whereas, 90% mice vaccinated with GroEL survive the lethal challenge of *S. typhimurium* (FIG. 5).

Method of development of the vaccine using Hsp of *Salmonella* is described hereinafter with an example, which is illustrative and is not intended to be taken restrictively to imply any limitation on the scope of the present invention.

Working Example-1

Genomic DNA is isolated from the overnight grown culture of *Salmonella typhi* using Genomic DNA isolation kit. GroEL (Hsp60) gene is amplified by PCR using Taq:Pfu (1:1). The PCR product is purified by PCR DNA purification kit.

Plasmid DNA of pQE-30 expression vector is isolated by miniprep kit. The PCR product and pQE-30 are restricted with Bam HI and Hind III to generate cohesive ends and are purified by Gel extraction. The PCR product of GroEL and pQE 30 vector DNA are then ligated at 16° C. overnight, using T4 DNA ligase. Transformation is carried out with ligated products using *E. coli* DH 5α cells and the resultant transformants are selected on Ampicillin plates.

Recombinants obtained are screened for the presence of desired insert by restriction digestion and PCR followed by sequencing. The recombinant plasmids are isolated and subsequently introduced into an expression strain of *E. coli* BL-21(DE-3) by electroporation. Briefly, electro-competent cells of BL-21 are prepared and electric shock of 1500 V is given to the mixture of cells in a medium containing recombinant plasmid DNA. Transformants are selected on ampicillin plates.

Overnight grown culture of recombinant BL 21 cell is induced with 0.5 mm IPTG for 3 h. The induced cell ($OD_{600}$~1.0) are lysed in native lysis buffer and incubated on ice for 30 min, followed by sonication on ice. Lysate is then centrifuged at 15,000 g for 20 min. To the pellet, lysis buffer containing 8M urea is added, incubated on ice for 30 min, and again sonicated as before. Lysate is centrifuged at 15,000 g for 20 min and supernatant is collected. The expression of protein is seen visualised by SDS PAGE followed by Western blotting using anti-histidine antibody as primary antibody and Rabbit anti-mouse Ipg-HRP conjugate as secondary antibody.

The recombination GroEL protein is purified by Ni-NTA chromatogramphy under denaturing conditions. Briefly, the protein sample is added to the charged gel and allowed to bind to the gel for 30 min at room temperature with gently agitation. The gel is pelleted by centrifugation at 500 g for 2 minutes and the supernatant is carefully decanted. The gel is washed with wash buffer 3 times and the protein is finally eluted with elution buffer using 0.5 M imidaole.

After purification, the protein is refolded in refolding buffer. Refolding is initiated by rapid dilution (10 times) of the purified protein (100 µg final concentrations) in refolding buffer (50 mM Tris; 1 mM EDTA; 1M arginine; 1 mM GSH; 0.8 mM GSSG, pH 7.5). Solution is kept stirring during dilution and is then incubated for 24 h at 4° C. without stirring. The refolded preparation is dialyzed extensively to eliminate arginine and urea, against dialysis buffer for 24 h, with buffer changes every 12 h. The dialyzed sample is centrifuged and concentrated by AMICON filtration.

The immune response of recombinant GroEL is evaluated by injecting (50 µg protein/mouse) intraperitonially on 0, 7$^{th}$ and 28$^{th}$ day. Seven days after the last injection, the mice are sacrificed and serum is collected for antibody titre. Antibody titre is determined by ELISA using 96-well microtitre plates previously coated with 1 µg of DnaK protein/well and blocked with BSA. Different dilutions (200 µl) of serum of immunized as well as unimmunized mice are added to the wells. After 2 h incubation at room temperature (RT), the wells are washed with PBS-Tween thrice and incubated with HRP conjugated goat anti-mouse IgG (at 1:2000 times dilution in PBS-Tween). After incubation for 1 hr at RT, the wells are washed as before and incubated with TMB substrate for 20-30 min at RT in dark. The colour development is terminated by addition of 50 µl 1N HCl and O.D. is read at 450 nm. A significant increase in antibody titre (>2,000,000) is observed in animals immunized with GroEL after third immunization (FIG. 1).

Lymphocyte proliferation is studied by Neutral Red assay. Briefly splenocytes from immunized and unimmunized (control) mice are incubated with (Induced) or without (uninduced) GroEL protein (20 µg/ml) or with heat killed *S. typhi* (20 µg/ml) in 96 well microtitre plates for 72 h. 10 µl of 0.1% Neutral Red is then added to each well. After incubation for 30 min at 37° C., the Cells are washed with PBS and 200 µl of ethanol:acetic acid (50:1) mixture is added. Supernatant is collected after centrifugation and colour obtained is measured at 570 nm. A significant increase in lymphocyte proliferation is observed in cells from immunized mice compared to unimmunized mice (FIG. 3). Further, there is an appreciable increase in γ-IFN and IL-4 production in lymphocytes isolated from immunized mice as compared to lymphocytes isolated from control mice. The study revealed that GroEL protein is highly immunogenic and stimulates both B and T lymphocytes.

Challenge and Protection Studies:

Eight to twelve week old female BALB/c mice are used in all cases. Mice (n=10) are vaccinated with GroEL (50 µg/mouse) on 0, 7$^{th}$ and 28$^{th}$ day. Two weeks after the last booster immunization, mice are challenged with *S. typhimurium* intraperitonially (1×10$^3$ cells/ml) to study the efficacy of GroEL as vaccine. The mice are monitored daily after infection for at least 2 months. All the control mice die within 48 hrs of challenge with *S. typhimurium*. However, 90% of mice vaccinated with GroEL survive the infection even after 60 days of challenge (FIG. 5).

Working Example-2

Genomic DNA is isolated from the overnight grown culture of *Salmonella typhi* using Genomic DNA isolation kit. DnaK gene is amplified by PCR using primers designed in the lab. Conditions of PCR are: 95° C. for 5 minutes (Pre heating lid), 95° C. for 1 minutes (denaturation), 55° C. for 1 minutes (annealing), 72° C. for 90 sec. (extension) for total of 36 cycles. The PCR product is purified by PCR DNA purification kit.

Plasmid DNA of pQE-30 expression vector is isolated by miniprep kit. The PCR product and pQE-30 are restricted with Bam HI and Hind III to generate cohesive ends and are purified by Gel extraction. The PCR product of DnaK and pQE 30 vector DNA are then ligated at 16° C. overnight, using T4 DNA ligase. Transformation is carried out with ligated products using *E. coli* DH 5α cells and the resultant transformants are selected on Ampicillin plates.

Recombinants obtained are screened for the presence of desired insert by restriction digestion and PCR followed by sequencing. The recombinant plasmids are isolated and subsequently introduced into an expression strain of *E. coli* BL-21 (DE-3) by electroporation. Briefly, electro-competent cells of BL-21 are prepared and electric shock of 1500 V is given to the mixture of cells in a medium containing recombinant plasmid DNA. Transformants are selected on ampicillin plates.

The recombinants *E. coli* BL-21 cells are grown overnight in LB medium at 37° C. The cells are then re-inoculated in fresh medium (1 L culture) and grown till $OD_{600}$ reached 0.5. The cells are induced with 0.5 mm IPTG ((isopropyl β-D-1-thiogalactopyranoside) for 3 h, lysed in native lysis buffer and incubated on ice for 30 min. The supernatant is collected and analyzed by SDS PAGE and Western blotting for the presence of recombinant protein. The DnaK protein is purified by Ni-NTA chromatography. Briefly, the protein sample is added to the charged gel and allowed to bind to gel for 30 min at room temperature with gentle agitation. Gel is sedimented by centrifugation at 500 g for 2 minutes and the supernatant is carefully decanted. The gel is washed with wash buffers and the protein is finally eluted with elution buffer containing 0.5M imidazole. The eluted protein is analyzed by SDS-PAGE followed by western blotting. The protein preparation is dialyzed extensively against dialysis buffer for 24 h, with buffer changes every 12 h. The dialyzed sample is centrifuged and concentrated by AMICON filtration.

The immune response of recombinant DnaK is evaluated by injecting (50 μg protein/mouse) intraperitonially on 0, $7^{th}$ and $28^{th}$ day. Seven days after the last injection, the mice are sacrificed and serum is collected for antibody titre. Antibody titre is determined by ELISA using 96-well microtitre plates previously coated with 1 μg of DnaK protein/well and blocked with BSA. A significant increase in antibody titre (2,000,000) is observed in animals immunized with DnaK after third immunization (FIG. 2).

The study revealed that DnaK protein is highly immunogenic and stimulates B lymphocytes.

Challenge and Protection Studies:

Eight to twelve week old female BALB/c mice are used in all cases. Mice (n=10) are vaccinated with DnaK (50 μg/mouse) on 0, $7^{th}$ and $28^{th}$ day. Two weeks after the last booster immunization, mice are challenged with *S. typhimurium* intraperitonially ($1\times10^5$ cells/ml) to study the efficacy of DnaK as vaccine. The mice are monitored daily after infection for at least 2 months. All the control mice die within 48 hrs of challenge with *S. typhimurium*. However, all the vaccinated mice survive the infection even after 60 days of challenge (FIG. 4).

The outline of the methodology adopted is shown in the form of flow chart.

FLOW CHART

Isolation of Genomic DNA from *S. typhi*

↓

-continued

Amplification of GroEL or DnaK gene by PCR

↓

Cloning of GroEL or DnaK gene into pQE-30 Expression Vector

↓

Transformation into E. coli BL21 strain

↓

Induction of recombinant protein by 0.5M IPTG

↓

Purification of protein by Ni-NTA chromatography

↓

Immunisation studies in mice

↓

Challenge studies with *S. typhimurium*

It is to be understood that the structure of the present invention is susceptible to modifications, changes and adaptations by those skilled in the art. Such modifications, changes and adaptations are intended to be within the scope of the present invention which is further set forth under the following claims.

The main advantages of the present invention are:

1. The present invention discloses a method to develop a potent vaccine against typhoid fever and salmonellosis in animals and humans using Hsp 60 or Hsp 70 protein of *S. typhi* and its closely related serovars.
2. The GroEL or DnaK based vaccine disclosed in the present invention stimulates both humoral and cell mediated immune responses and is currently not available against microbial infections.
3. The vaccine disclosed in the present invention is free from unpleasant side effects and toxicity.
4. The vaccine which can be mass produced in short time.
5. Development of the vaccine against typhoid fever and salmonellosis as disclosed in the present invention has no ethical problems.
6. The method used in the present invention is cost effective and economical compared to the prior art. The running cost is also very low.

We claim:

1. A vaccine comprising one or more heat shock proteins (Hsp) of *Salmonella typhi* or its closely related serovars that elicits protective immunological responses in a host wherein said Hsp is GroEL protein or DnaK protein and wherein said Hsp is purified using Ni-NTA chromatography, and said closely related serovars consist of serovars related to *Salmonella typhi* having one or more Hsps that elicit a protective immune response against typhoid fever and salmonellosis.

2. The vaccine as claimed in claim 1 further comprising one or more antigenic molecules.

3. The vaccine as claimed in claim 2 wherein said Hsp is bound to an antigenic molecule covalently or non-covalently.

4. The vaccine as claimed in claim 2 wherein said antigenic molecule is exogenous antigen or exogenous immunogen selected from a group consisting of lipo-polysaccharides, peptides, nucleic acids, polysaccharides, antigenic fragments, immunogenic fragments and derivatives thereof.

5. A method for vaccinating a mammal against typhoid fever which comprises administering to the mammal an amount of the vaccine as claimed in claim 1, sufficient to elicit a protective immune response in the mammal.

6. The method as claimed in claim 5 wherein said Hsp is administered to a mammal in an amount in the range of 1-100 μg/kg body weight of said mammal.

7. The vaccine composition as claimed in claim 1 further comprising one or more pharmaceutically acceptable additives.

8. The vaccine composition as claimed in claim 7 wherein said pharmaceutically acceptable additives are selected from the group consisting of carriers, diluents, stabilizing agents, solvents, flavoring agents, binders, and lubricants and a mixture thereof.

9. A method of preparing a vaccine comprising one or more Hsps of *Salmonella typhi* or its closely related serovars wherein said Hsp is GroEL protein or DnaK protein, and said closely related serovars consist of serovars related to *Salmonella typhi* having one or more Hsps that elicit a protective immune response against typhoid fever and salmonellosis, the method comprising the steps of:
 (a) isolating and amplifying GroEL gene or DnaK gene:
 (b) cloning of genomic DNA from GroEL or DnaK into expression vector to obtain recombinant plasmids;
 (c) transformation of said recombinant plasmids into *E. coli* to obtain recombinant *E. coli* cells; and
 (d) inducing and purifying recombinant protein from said recombinant *E. coli* cells using Ni-NTA chromatography.

10. The vaccine composition as claimed in claim 2 further comprising one or more pharmaceutically acceptable additives.

11. The vaccine composition as claimed in claim 4 further comprising one or more pharmaceutically acceptable additives.

12. A method for vaccinating a mammal against salmonellosis which comprises administering to the mammal an amount of the vaccine as claimed in claim 1, sufficient to elicit a protective immune response in the mammal.

* * * * *